United States Patent
Markham et al.

(10) Patent No.: US 9,855,008 B2
(45) Date of Patent: Jan. 2, 2018

(54) DIRECT INTEGRATION OF FEEDTHROUGH TO IMPLANTABLE MEDICAL DEVICE HOUSING WITH ULTRASONIC WELDING

(71) Applicant: Heraeus Deutschland GmbH & Co. KG, Hanau (DE)

(72) Inventors: Jacob Markham, Vadnais Heights, MN (US); Ulrich Hausch, Frankfurt (DE)

(73) Assignee: Heraeus Deutschland GmbH & Co. LG, Hanau (DE)

( * ) Notice: Subject to any disclaimer, the term of this patent is extended or adjusted under 35 U.S.C. 154(b) by 0 days.

(21) Appl. No.: 15/363,886

(22) Filed: Nov. 29, 2016

(65) Prior Publication Data

US 2017/0071542 A1   Mar. 16, 2017

Related U.S. Application Data

(62) Division of application No. 14/104,644, filed on Dec. 12, 2013, now Pat. No. 9,504,841.

(51) Int. Cl.
  *A61N 5/00*   (2006.01)
  *A61B 5/00*   (2006.01)
  (Continued)

(52) U.S. Cl.
  CPC .............. *A61B 5/6847* (2013.01); *A61N 1/36* (2013.01); *A61N 1/3754* (2013.01);
  (Continued)

(58) Field of Classification Search
  CPC .............................. A61N 1/3754; B23K 20/10
  See application file for complete search history.

(56) References Cited

U.S. PATENT DOCUMENTS 3,065,533 A   11/1962   Dungan et al.
3,979,187 A   9/1976   Scherer
(Continued)

FOREIGN PATENT DOCUMENTS

DE   69729719   7/2005
DE   102006054249   5/2008
(Continued)

OTHER PUBLICATIONS

Exner, Horst et al., "Laser Joining of Ceramics in Liquid Phase," pp. 1-8 (Nov. 8, 2011).
(Continued)

*Primary Examiner* — Alyssa M Alter
(74) *Attorney, Agent, or Firm* — Dicke, Billig & Czaja, PLLC

(57) ABSTRACT

One aspect is an implantable medical device including a metal housing configured for implantation in a human and including a biocompatible metal and defining an opening. A feedthrough device is configured within the opening of the metal housing and includes an insulating section and a conducting section, the insulating section electrically isolating the conducting section from the metal housing. An ultrasonic joint is configured between the feedthrough device and metal housing that hermetically and mechanically bonds the feedthrough device and metal housing. The biocompatible metal of the housing is a microstructure primarily having α-phase grains.

17 Claims, 5 Drawing Sheets

(51) Int. Cl.
*A61N 1/375* (2006.01)
*B23K 20/00* (2006.01)
*B23K 20/10* (2006.01)
*B23K 1/00* (2006.01)
*B23K 20/16* (2006.01)
*B23K 20/233* (2006.01)
*A61N 1/36* (2006.01)
*B23K 101/42* (2006.01)
*B23K 101/36* (2006.01)
*B23K 103/14* (2006.01)

(52) U.S. Cl.
CPC .......... *B23K 1/0016* (2013.01); *B23K 20/002* (2013.01); *B23K 20/10* (2013.01); *B23K 20/16* (2013.01); *B23K 20/233* (2013.01); *B23K 2201/36* (2013.01); *B23K 2201/42* (2013.01); *B23K 2203/14* (2013.01)

(56) References Cited

U.S. PATENT DOCUMENTS

| | | |
|---|---|---|
| 4,152,540 A | 5/1979 | Duncan et al. |
| 4,217,137 A | 8/1980 | Kraska et al. |
| 4,315,054 A | 2/1982 | Sack et al. |
| 4,352,951 A | 10/1982 | Kyle |
| 4,354,964 A | 10/1982 | Hing et al. |
| 4,362,792 A | 12/1982 | Bowsky et al. |
| 4,456,786 A | 6/1984 | Kyle |
| 4,488,673 A | 12/1984 | Hopper, Jr. |
| 4,602,956 A | 7/1986 | Partlow et al. |
| 4,678,868 A | 7/1987 | Kraska et al. |
| 4,737,601 A | 4/1988 | Gartzke |
| 4,774,953 A | 10/1988 | Foote |
| 4,816,621 A | 3/1989 | Huebner et al. |
| 4,991,582 A | 2/1991 | Byers et al. |
| 4,992,910 A | 2/1991 | Evans |
| 5,043,535 A | 8/1991 | Lin |
| 5,046,262 A | 9/1991 | Kerbaugh |
| 5,245,999 A | 9/1993 | Dahlberg et al. |
| 5,272,283 A | 12/1993 | Kuzma |
| 5,333,095 A | 7/1994 | Stevenson et al. |
| 5,393,568 A | 2/1995 | Valente et al. |
| 5,407,119 A | 4/1995 | Churchill et al. |
| 5,408,066 A | 4/1995 | Trapani et al. |
| 5,513,793 A | 5/1996 | Malmgren |
| 5,515,604 A | 5/1996 | Horine et al. |
| 5,587,111 A | 12/1996 | Watanabe et al. |
| 5,648,302 A | 7/1997 | Brow et al. |
| 5,654,106 A | 8/1997 | Purnell et al. |
| 5,683,435 A | 11/1997 | Truex et al. |
| 5,738,270 A | 4/1998 | Malmgren |
| 5,750,926 A | 5/1998 | Schulman et al. |
| 5,756,408 A | 5/1998 | Terashi et al. |
| 5,769,874 A | 6/1998 | Dahlberg |
| 5,782,891 A | 7/1998 | Hassler et al. |
| 5,796,019 A | 8/1998 | Lupton et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 5,870,272 A | 2/1999 | Seifried et al. |
| 5,905,627 A | 5/1999 | Brendel et al. |
| 6,031,710 A | 2/2000 | Wolf et al. |
| 6,093,476 A | 7/2000 | Horiuchi et al. |
| 6,232,004 B1 | 5/2001 | Lasater |
| 6,284,080 B1 | 9/2001 | Haq et al. |
| 6,414,835 B1 | 7/2002 | Wolf et al. |
| 6,579,492 B2 | 6/2003 | Wehler |
| 6,586,675 B1 | 7/2003 | Bealka et al. |
| 6,643,903 B2 | 11/2003 | Stevenson et al. |
| 6,660,116 B2 | 12/2003 | Wolf et al. |
| 6,999,818 B2 | 2/2006 | Stevenson et al. |
| 7,035,076 B1 | 4/2006 | Stevenson |
| 7,038,900 B2 | 5/2006 | Stevenson et al. |
| 7,068,491 B1 | 6/2006 | Burdon et al. |
| 7,107,099 B1 | 9/2006 | O'Phelan et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,222,419 B2 | 5/2007 | Horng et al. |
| 7,260,434 B1 | 8/2007 | Lim et al. |
| 7,274,963 B2 | 9/2007 | Spadgenske |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,569,452 B2 | 8/2009 | Fu et al. |
| 7,630,768 B1 | 12/2009 | Coffed et al. |
| 7,668,597 B2 | 2/2010 | Engmark et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,155,743 B2 | 4/2012 | Rundle et al. |
| 8,163,397 B2 | 4/2012 | Ok et al. |
| 8,179,658 B2 | 5/2012 | Brendel et al. |
| 8,189,333 B2 | 5/2012 | Foster |
| 8,288,654 B2 | 10/2012 | Taylor et al. |
| 8,346,362 B2 | 1/2013 | Kinney et al. |
| 8,355,785 B1 | 1/2013 | Hammond et al. |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,552,311 B2 | 10/2013 | Koester et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,755,887 B2 | 6/2014 | Troetzschel et al. |
| 8,825,162 B2 | 9/2014 | Reisinger |
| 8,886,320 B2 | 11/2014 | Troetzschel et al. |
| 8,894,914 B2 | 11/2014 | Pavlovic |
| 8,929,987 B2 | 1/2015 | Troetzschel et al. |
| 9,504,841 B2 | 11/2016 | Markham et al. |
| 9,610,451 B2 | 4/2017 | Markham et al. |
| 9,610,452 B2 | 4/2017 | Markham et al. |
| 2001/0013756 A1 | 8/2001 | Mori et al. |
| 2001/0018012 A1 | 8/2001 | Harmand et al. |
| 2001/0041227 A1 | 11/2001 | Hislop |
| 2002/0166739 A1 | 11/2002 | Naerheim |
| 2003/0109903 A1 | 6/2003 | Berrang et al. |
| 2003/0123215 A1 | 7/2003 | Allen et al. |
| 2004/0023101 A1 | 2/2004 | Jacobson et al. |
| 2004/0116976 A1 | 6/2004 | Spadgenske |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2006/0259093 A1 | 11/2006 | Stevenson et al. |
| 2007/0041164 A1 | 2/2007 | Greenberg et al. |
| 2007/0183118 A1 | 8/2007 | Fu et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0269831 A1 | 10/2008 | Erickson |

(56) References Cited

U.S. PATENT DOCUMENTS

| | | |
|---|---|---|
| 2009/0079517 A1 | 3/2009 | Iyer |
| 2009/0192578 A1 | 7/2009 | Biggs |
| 2009/0281586 A1 | 11/2009 | Lim |
| 2009/0309459 A1 | 12/2009 | Ogashiwa et al. |
| 2010/0022861 A1* | 1/2010 | Cinbis ............ A61B 5/0084 600/325 |
| 2010/0023086 A1 | 1/2010 | Lim |
| 2010/0109966 A1 | 5/2010 | Mateychuk et al. |
| 2010/0121438 A1 | 5/2010 | Jarvik |
| 2010/0241206 A1 | 9/2010 | Truex et al. |
| 2010/0258342 A1 | 10/2010 | Parker |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0106228 A1 | 5/2011 | Reiterer et al. |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |
| 2012/0006576 A1 | 1/2012 | Barry et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2012/0319319 A1 | 12/2012 | Parker et al. |
| 2013/0035733 A1* | 2/2013 | Breyen ............ A61N 1/3754 607/2 |
| 2013/0060312 A1 | 3/2013 | Iyer et al. |
| 2013/0070387 A1 | 3/2013 | Stevenson et al. |
| 2013/0127567 A1 | 5/2013 | Iyer et al. |
| 2013/0138186 A1 | 5/2013 | Iyer et al. |
| 2013/0138187 A1 | 5/2013 | Iyer et al. |
| 2013/0184796 A1 | 7/2013 | Marzano et al. |
| 2013/0184797 A1 | 7/2013 | Tang et al. |
| 2013/0286536 A1 | 10/2013 | Iyer et al. |
| 2013/0299233 A1 | 11/2013 | Troetzschel et al. |
| 2014/0008121 A1 | 1/2014 | Troetzschel et al. |
| 2014/0144014 A1 | 5/2014 | Troetzschel et al. |
| 2014/0262494 A1 | 9/2014 | Reisinger et al. |
| 2014/0318956 A1 | 10/2014 | Okamoto et al. |
| 2014/0345934 A1 | 11/2014 | Markham et al. |
| 2014/0368298 A1 | 12/2014 | Reisinger |
| 2014/0371835 A1 | 12/2014 | Powell et al. |
| 2015/0165218 A1 | 6/2015 | Markham et al. |
| 2015/0165219 A1 | 6/2015 | Markham et al. |
| 2015/0165220 A1 | 6/2015 | Markham et al. |
| 2017/0203106 A1 | 7/2017 | Markham et al. |
| 2017/0203107 A1 | 7/2017 | Markham et al. |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| DE | 102011119125 | 5/2013 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| WO | 03073450 | 9/2003 |
| WO | 2004110555 | 12/2004 |
| WO | 2008103166 | 8/2008 |
| WO | 2010091435 | 8/2010 |
| WO | 2011053540 | 5/2011 |
| WO | 2012110242 | 8/2012 |
| WO | 2012110245 | 8/2012 |
| WO | 2013075797 | 5/2013 |

OTHER PUBLICATIONS

Hussain, et al., "Electrical conductivity of an insulator matrix (alumina) and conductor particle (molybdenum) composites", Journal of the European Ceramic Society, vol. 23, Issue 2, Feb. 2003, pp. 315-321.

Gil et al., "Grain Growth Kinetics of Pure Titanium," Scripta Metallurgica et Materialia, vol. 33, No. 8, pp. 1361-1366 (1995).

The International Search Report and the Written Opinion for International Application No. PCT/IB2014/066773 dated Mar. 31, 2015 (12 pages).

The International Search Report and the Written Opinion for International Application No. PCT/IB2014/066774 dated May 6, 2015 (13 pages).

The International Search Report and the Written Opinion for International Application No. PCT/IB2014/066775 dated Feb. 19, 2015 (12 pages).

The Restriction Requirement for U.S. Appl. No. 14/104,636 dated Apr. 17, 2015 (5 pages).

The Office Action for U.S. Appl. No. 14/104,636 dated Jul. 20, 2015 (36 pgs).

Bulletin of Alloy Phase Diagrams, 1980, vol. 1, No. 2, p. 51-54.

The Final Office Action for U.S. Appl. No. 14/104,636 dated Dec. 7, 2015 (25 pages).

Alloy Data, Ti-6AI-4V, Carpenter technology corp., 2000, p. 1-2.

The Advisory Action for U.S. Appl. No. 14/104,636 dated Feb. 18, 2016 (4 pages).

The Office Action for U.S. Appl. No. 14/104,636 dated Jul. 8, 2016 (15 pages).

The Final Office Action for U.S. Appl. No. 14/104,636 dated Nov. 9, 2016 (12 pages).

The Restriction Requirement for U.S. Appl. No. 14/104,644 dated Jun. 3, 2015 (7 pages).

The Office Action for U.S. Appl. No. 14/104,644 dated Jul. 31, 2015 (29 pgs).

The Final Office Action for U.S. Appl. No. 14/104,644 dated May 5, 2016 (13 pages).

The Notice of Allowance for U.S. Appl. No. 14/104,644 dated Aug. 18, 2016 (11 pages).

The Restriction Requirement for U.S. Appl. No. 14/104,653 dated Jun. 26, 2015 (7 pages).

The Office Action for U.S. Appl. No. 14/104,653 dated Sep. 10, 2015 (46 pages).

The Final Office Action for U.S. Appl. No. 14/104,653 dated May 17, 2016 (21 pages).

The Notice of Allowance for U.S. Appl. No. 14/104,636 dated Jan. 23, 2017 (6 pgs).

The Notice of Allowance for U.S. Appl. No. 14/104,653 dated Jan. 18, 2017 (11 pgs).

The Office Action for U.S. Appl. No. 15/476,716 dated Jun. 21, 2017 (36 pgs).

* cited by examiner

DIRECT INTEGRATION OF FEEDTHROUGH TO IMPLANTABLE MEDICAL DEVICE HOUSING WITH ULTRASONIC WELDING

CROSS-REFERENCE TO RELATED APPLICATIONS

This application is a divisional of U.S. patent application Ser. No. 14/104,644, entitled "DIRECT INTEGRATION OF FEEDTHROUGH TO IMPLANTABLE MEDICAL DEVICE HOUSING WITH ULTRASONIC WELDING," having a filing date of Dec. 12, 2013, which is incorporated herein by reference.

This patent application is related to Ser. No. 14/104,636, filed Dec. 12, 2013, entitled "DIRECT INTEGRATION OF FEEDTHROUGH TO IMPLANTABLE MEDICAL DEVICE HOUSING USING A GOLD ALLOY" having and Ser. No. 14/104,653, filed Dec. 12, 2013, entitled "DIRECT INTEGRATION OF FEEDTHROUGH TO IMPLANTABLE MEDICAL DEVICE HOUSING BY SINTERING", all of which are incorporated herein by reference.

BACKGROUND

Implantable medical devices, such as cardiac pacemakers, cardiac defibrillators, and neurostimulators, receive and/or deliver electrical signals to/from portions of the body via sensing and/or stimulating leads. Implantable medical devices typically include a metal housing (typically titanium) having a hermetically sealed interior space which isolates the internal circuitry, connections, power sources, and other device components from body fluids. A feedthrough device (often referred to simply as a feedthrough) establishes electrical connections between the hermetically sealed interior space and the exterior bodily fluid side of the device.

Feedthroughs typically include an insulator (typically ceramic) and electrical conductors or feedthrough pins which extend through the insulator to provide electrical pathways between the exterior and the hermetically sealed interior. A frame-like metal ferrule is disposed about a perimeter surface of the insulator, with the ferrule and insulator typically being joined to one another via a brazing or soldering process. The ferrule is configured to fit into a corresponding opening in the metal housing, with the ferrule being mechanically and hermetically attached to the housing, typically via laser welding. The insulator electrically insulates the feedthrough pins from one another and from the metal ferrule/housing.

The ferrule is typically joined to insulator via a welding or brazing process. However, the high temperatures employed by such processes heats the titanium of the housing about the perimeter of the opening to levels that cause a structural change in the titanium, commonly referred to as "grain growth". This structural change can distort the dimensions of the opening and cause the titanium about the perimeter of the opening to become less rigid, each of which can result in a weaker joint between the ferrule and the housing.

Additionally, machining the ferrule (typically from pure titanium) to provide a high tolerance gap between the ferrule and the insulator (about 10-50 µm) which is necessary to achieve a quality braze joint is demanding and costly. Furthermore, if the gap is not maintained during the brazing process, or if the brazing process itself is not properly performed, a weak joint may be formed that can lead to premature failure of the implantable device.

For these and other reasons there is a need for the embodiments of the present disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
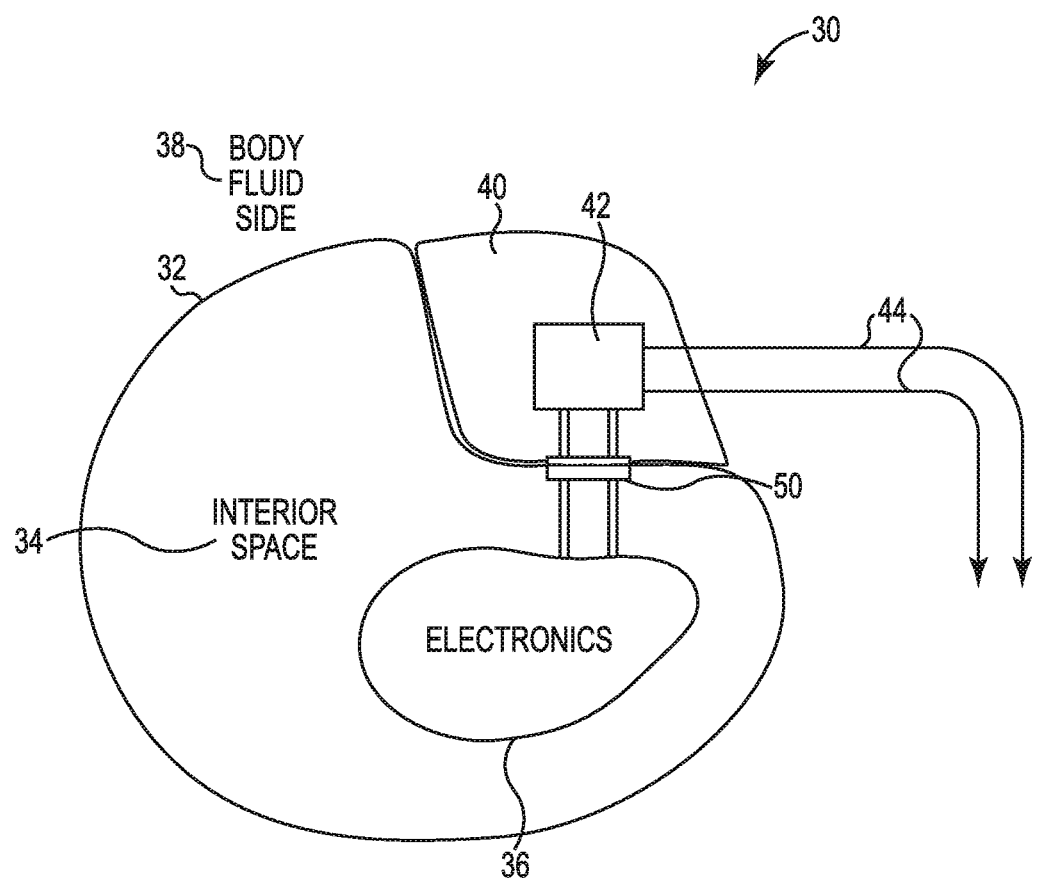
FIG. 1 generally illustrates an example of an implantable medical device according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment is a method of securing a feedthrough to a metal housing for an implantable medical device. The method provides the feedthrough including an insulating section and at least one conductive section extending through the insulating section. At least a portion of the insulating section is metalized. The metalized feedthrough is placed within an opening in the metal housing of the implantable medical device. The feedthrough and metal housing are positioned within an ultrasonic welding system. The ultrasonic welding system is energized such that ultrasonic energy welds the feedthrough directly to the metal housing. The temperature of the metal housing is not raised above the β-transus temperature of the metal housing during the ultrasonic welding.

Accordingly, significant heat is avoided in securing the feedthrough directly to the metal housing thereby avoiding structural changes in the metal housing. Where the housing is a metal, such as titanium, avoiding significant heating levels prevents grain growth in the titanium, which can cause undesirable dimensional changes, cause perimeter areas of openings to become less rigid and lead to a weakened or defective joint.

In one embodiment, the method includes positioning the feedthrough and metal housing within the ultrasonic welding system and further positioning the feedthrough and metal housing between a first portion and a second portion of the ultrasonic welding system and such that the first portion contacts only the feedthrough on a first side and the second portion contacts only the metal housing on a second side opposite the first side as the first and second portions of the ultrasonic welding system are forced together.

Forcing the feedthrough on one side against the metal housing with a force the opposite side creates a force at the interface between the feedthrough and housing thereby facilitating a high-quality ultrasonic joint between them.

In one embodiment, the method further includes placing a bond material between the metalized feedthrough and the metal housing such that the temperature of the metal housing, the metalized feedthrough, and the bonding material is not raised above the β-transus temperature of the metal housing and the metalized feedthrough during the ultrasonic welding. Avoiding high temperatures while securing the feedthrough directly to the metal housing, also avoids structural changes in the metal housing and leads to a superior joint.

In one embodiment, the method is used wherein the temperature of the metal housing is kept below 890° C. while the ultrasonic welding system is energized and the feedthrough is welded to the metal housing, and in another, the temperature of the metal housing is kept below 750° C. Again, avoiding high temperatures avoids structural changes in the metal housing and leads to a superior joint.

In one embodiment, the method is used wherein the temperature of the metal housing is controlled while the ultrasonic welding system is energized and the feedthrough is welded to the metal housing such that the metal housing does not experience significant grain growth. In another, the temperature is controlled such that the microstructure of the metal housing remains primarily α-phase grains having an average grain size of less than 425 μm and in another embodiment, such that the microstructure of the metal housing remains primarily α-phase grains having an average grain size in the range of 10-40 μm. Avoiding significant heat levels while securing the feedthrough directly to the metal housing, avoids structural changes in the metal housing and leads to a superior ultrasonic joint between the feedthrough and metal housing.

In one embodiment, an implantable medical device includes a metal housing configured for implantation in a human and a biocompatible metal and defining an opening. A feedthrough device is configured within the opening of the metal housing and includes an insulating section and a conducting section, the insulating section electrically isolating the conducting section from the metal housing. An ultrasonic joint is made between the feedthrough device and metal housing that hermetically and mechanically bonds the feedthrough device and metal housing. The biocompatible metal of the housing has a microstructure primarily having α-phase grains.

Accordingly, since the biocompatible metal of the housing is primarily α-phase grains that are smaller grains and, thus, more grain boundaries, are harder than metals having larger grains, which have fewer grain boundaries. As a result, the primarily α-phase smaller grains are a close-packed hexagonal crystal structure, which allows for less dimensional changes thereby leading to a superior ultrasonic joint between the feedthrough device and metal housing.

In one embodiment, the implantable medical device is further characterized in that the biocompatible metal of the housing comprises a microstructure having substantially no β-phase grains. Because β-phase grains are larger than α-phase, the β-phase grains can cause dimensional distortions in the metal housing. Avoiding this leads to a more rigid perimeter of the opening and a better seal being formed between the housing and the feedthrough.

In one embodiment, the implantable medical device further includes a biocompatible bonding material between the feedthrough device and metal housing to help create a strong ultrasonic joint therebetween. In one embodiment, the implantable medical device has a metal housing of titanium, niobium or a combination thereof.

In one embodiment, the implantable medical device has a metal housing with a metal having an average grain size less than 300 μm, in one case an average grain size less than 100 μm, and in one case an average grain size in the range of 10-40 μm. Because of the smaller grain sizes, the grains are close-packed, which allows for less dimensional changes in the housing, thereby leading to a superior ultrasonic joint between the feedthrough device and metal housing.

In one embodiment, an interface between the feedthrough and metal housing is substantially angled relative an exterior surface of the metal housing. The angled exterior surfaces facilitate forcing the feedthrough against the metal housing causing a force at the interface between the feedthrough and housing thereby facilitating a high-quality ultrasonic joint between them.

In one embodiment, the implantable medical device has a width on the opening of the housing that is smaller than a width of the feedthrough device at its widest distance between two opposing sides. The overlap caused by the difference in width between the housing and the feedthrough device facilitates the welding of a high-quality ultrasonic joint between them.

In one embodiment, an implantable medical device includes a housing having an opening with an opening width. A feedthrough includes an insulator having a bottom surface and side surfaces and having an insulator width between opposing side surfaces that is greater than the opening width. An ultrasonic joint between at least one of the bottom surface, top surface, and side surfaces of the insulator and the housing hermetically seals the insulator to the housing.

In one case, the overlap caused by the difference in width between the housing and the feedthrough device facilitates the welding of a high-quality ultrasonic joint between them.

In one embodiment, the implantable medical device has an insulator width between opposing side surfaces that is two times greater than the opening width. This allows sufficient space for the welding of a high-quality ultrasonic joint between them.

In one embodiment, the implantable medical device has a housing that is a biocompatible metal with a microstructure primarily having α-phase grains, and in one case has a microstructure having substantially no β-phase grains and in one case has an average grain size less than 300 µm. Because of the smaller grain sizes, the grains are close-packed, which allows for less dimensional changes in the housing, thereby leading to a superior ultrasonic joint between the feedthrough device and metal housing.

FIG. 1 is a block and schematic diagram generally illustrating one embodiment of an implantable medical device 30, such as a cardiac pacemaker for example. Implantable medical device 30 includes a hermetically sealed metal case or housing 32, typically formed of titanium, which defines a hermetically sealed interior space 34 in which device electronics 36 are disposed and protected from fluids of the body fluid side 38 external to housing 32. A header 40 attaches to housing 32 and includes a connector block 42, which typically includes one or more sockets for connecting to one or more sensing and/or stimulating leads 44 that extend between implantable medical device 30 and desired regions of the body, such as the human heart and brain, for example. A feedthrough device 50 establishes electrical pathways or connections through housing 32 that maintain the integrity of hermetically sealed interior space 34 and provide electrical connection of leads 44 to internal device electronics 36.

Figure 2:
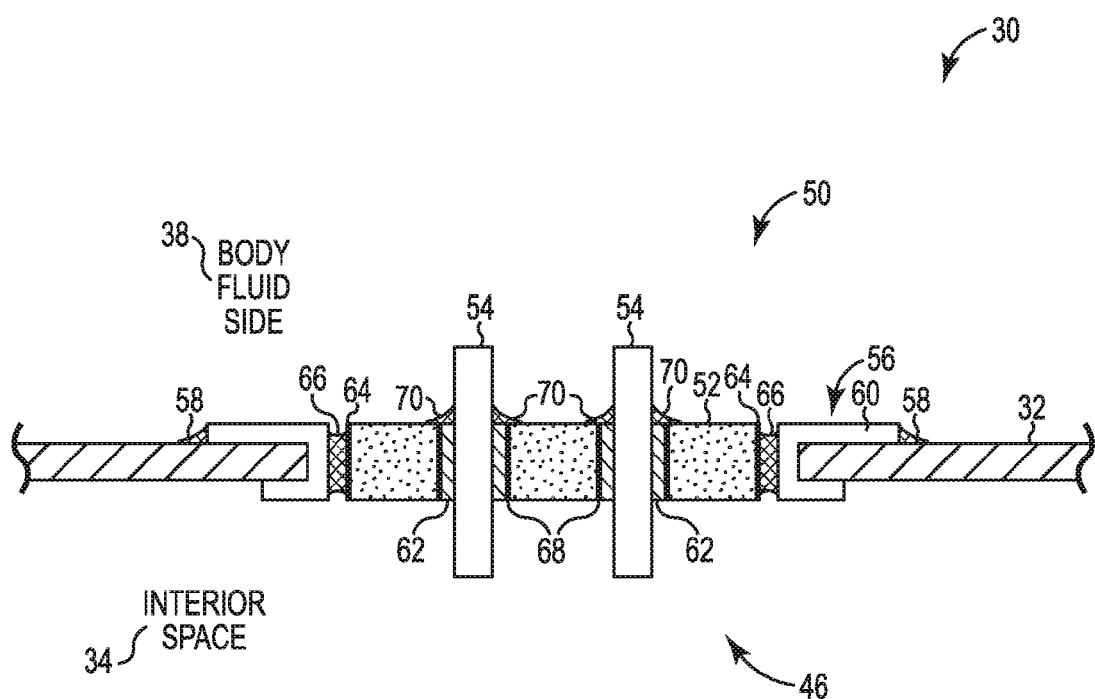
FIG. 2 illustrates a feedthrough device in an implantable in accordance with the prior art.

FIG. 2 is a cross-sectional view illustrating portions of an implantable medical device, such as medical device 30 of FIG. 1, including metal housing 32 having an opening 46 in which a conventional feedthrough device 50 is positioned. Feedthrough device 50 includes an insulator 52, feedthrough pins or conducting elements 54, and a ferrule 56. Ferrule 56 is a frame-like metal structure that holds insulator 52 and which is configured to fit into opening 46 for attachment to housing 32. Ferrule 56 is a bio-compatible material, typically titanium, which is mechanically and hermetically attached to housing 32 by laser welds 58, or similar techniques. Ferrule 56, as illustrated in FIG. 2, sometimes includes a flange 60 to further aid in securing ferrule 56 to housing 32.

Conducting elements 54 extend through openings or vias 62 in insulator 52 and are formed of an electrically conductive material so as to provide electrically conductive pathways from the external body fluid side 38 of housing 32 to hermetically sealed interior space 34. Insulator 52 is formed of a non-electrically conductive material, such as a ceramic material, aluminum oxide ($Al_2O_3$) for example, and electrically isolates conducting elements 54 from one another and from ferrule 56 and housing 32.

When attaching insulator 52 and ferrule 56 to one another, a perimeter surface of insulator 52 is typically metalized (through a sputter coating process, for example) to provide a thin metal coating 64 thereon. Ferrule 56 is then joined to insulator 52 via metal coating 64 using a braze 66, such as of gold, for example, to form a biocompatible and hermetic seal. Similarly, interior surface of vias 62 are provided with a metal coating 68 and a braze 70 (e.g. gold) is used to couple conducting elements 54 to insulator 52 and form a biocompatible and hermetic seal.

In order to achieve a quality braze, and thereby a quality hermetic seal, a proper gap must be maintained between ferrule 56 and insulator 52 during the brazing process (typically about 10-50 um) so that the brazing material (e.g. gold) is properly drawn into the gap by capillary action to create a strong and reliable braze 66. Forming ferrule 56, typically via machining processes, to meet the tight tolerances required to provide the proper gap with insulator 52 as well as to the dimensions of opening 46 in housing 42 is time consuming and costly. Also, during the brazing process, intermetallics are formed between the brazing material (e.g. gold) and the material (e.g. titanium) of ferrule 56, with the intermetallics being brittle as compared to the brazing material. If the gap between ferrule 56 and insulator 52 is too small, the amount of intermetallics may be large relative to the amount of pure brazing material (e.g. gold) resulting in a brittle braze 66 that may crack and comprise the hermitic seal.

Additionally, heat from the brazing (or welding) of ferrule 56 to housing 32 can cause structural changes in the titanium of housing 32 about opening 46 (and to ferrule 56) due to "grain growth" in the titanium. Such "grain growth" can cause undesirable dimensional changes in opening 46 and can cause the titanium about the perimeter of opening 46 to become less rigid (i.e. more flexible), which such changes leading to a weakened or defective joint.

All polycrystalline materials, including titanium, are made of closely packed atoms, with "regions of regularity" within these closely packed atoms (i.e. where the atoms have a regular structure, such as 8-co-ordination and 12-co-ordination, for example) being referred to as "crystal grains". Metal consists of a vast number of these crystal grains. The boundaries of these crystals (i.e. "grain boundaries") are locations at which atoms have become misaligned (i.e. the regular structure is discontinuous). Metals having smaller grains and, thus, more grain boundaries, are harder than metals having larger grains, which have fewer grain boundaries and, as a result, are softer and more flexible.

Heating of a metal, such as titanium, causes the atoms to move into a more regular arrangement, thereby decreasing the overall number of crystal grains but increasing the grain size of the remaining grains (i.e. the number of grains per unit volume decreases). The process by which the average grain size increases, so-called "grain growth", rearranges the crystalline structure of the metal and can cause dimensional changes (i.e. dimensional deformation) of the metal and cause the metal to become more flexible.

Titanium has an α-phase, which has a close-packed hexagonal crystal structure, and a β-phase, which has centered-cubic crystal structure and that is more open and prone to grain growth than the hexagonal structure. Titanium transitions from α-phase to β-phase, the so-called β-transus, when heated to or above a certain temperature, referred to as the β-transus temperature. The β-transus temperature is affected by impurities in the titanium (e.g. iron, carbon, hydrogen), but typically occurs at about 880° C. in commercially-pure titanium. Commercially pure titanium, as opposed to titanium alloys having additive such as aluminum (Al), typically has a microstructure of primarily α-phase grains having an average grain size in the range of 10-40 µm.

The grain growth of a metal, including titanium, is a function of the time and temperature for which a metal is heated. For example, while the average grain size of commercially-pure titanium increases when heated to temperatures below the β-transus temperature, such grain growth accelerates rapidly when the titanium is heated to a temperature at or above the β-transus temperature and the titanium transitions from α-phase to β-phase. For instance, the average grain size of commercially-pure titanium has been shown to increase in from about 10-40 µm to about 70 µm when heated at 700° C. for 120 minutes, to about 100 µm when heated at 750° C. for 120 minutes, and to about 180 µm when heated at 800° C. for 120 minutes. However, the average grain size of commercially-pure titanium has been shown to increase in from about 10-40 µm to about 350 µm when heated at 1000° C. for 120 minutes, and to about 425 µm when heated at 1100° C. for 120 minutes.

With reference to conventional feedthrough 50 of FIG. 2, attaching ferrule 56 to housing 32 by laser welding or brazing (e.g. gold braze) heats housing 32 to a temperature well above the β-transus temperature of titanium, resulting in rapid grain growth in the titanium of housing 32. For example, the average grain size may increase by 300 µm or more. Such grain growth causes dimensional distortions in housing 32 that can cause opening 46 to be outside of specified tolerances and causes the titanium about the perimeter of opening 46 to become less rigid, each of which can result in a poor or defective seal being formed between housing 32 and feedthrough 50.

Figure 3:
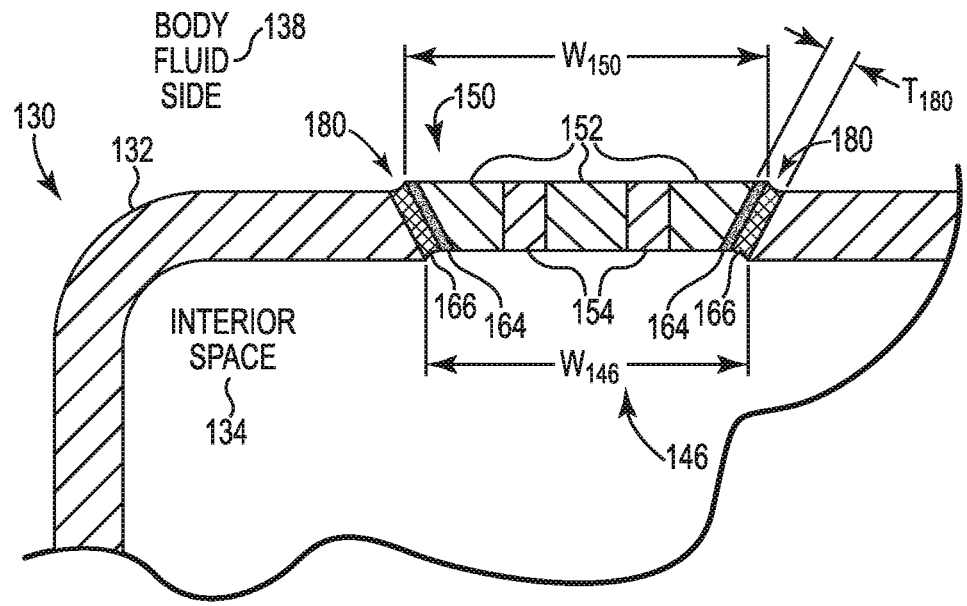
FIG. 3 illustrates a cross-sectional view of a feedthrough in an implantable medical device in accordance with one embodiment.

FIG. 3 is a schematic diagram illustrating portions of an implantable medical device 130, including a housing 132 and feedthrough 150 according to one embodiment of the present disclosure. As will be described in greater detail below, insulator 152 of feedthrough 150 is attached directly to housing 132 with a bond material 166 using ultrasonic welding to form an ultrasonic joint 180 that is formed at a low-temperature, which is at least at temperatures below the β-transus temperature of the titanium of housing 132.

By attaching feedthrough 150 directly to housing 132 via insulator 152, the need for a ferrule (such as ferrule 56 of FIG. 2) is eliminated, thereby eliminating the cost of manufacturing such a ferrule as well as the difficulties and shortcomings associated with attaching such a ferrule to the insulator (such as insulator 52 of FIG. 2). Additionally, by attaching feedthrough 150 to housing 132 using ultrasonic welding at reduced temperatures relative to conventional welding or brazing techniques, dimensional distortions of housing 132 due to the high temperatures and grain growth of titanium are substantially reduced, at least to levels that maintain dimensions of housing 132 within specified tolerances, and the titanium remains in a more rigid state.

While FIG. 3 is a cross-sectional view illustrating portions of housing 132, particularly the location where feedthrough 150 attaches to housing 132 to seal opening 146, implantable medical device 130 may include additional features similar to those described with respect to medical device 30 of FIG. 1. According to one embodiment, housing 132 is formed of titanium and defines a hermetically sealed interior space 134 in which device electronics 136 are disposed and protected from fluids of body fluid side 138 external to housing 132. According to one embodiment, a header, similar to header 40 of FIG. 1, for example, may also be provided to attach to housing 132, and in some instances includes a connector block, which typically includes one or more sockets for connecting to one or more sensing and/or stimulating leads.

Similar to that described above with regard to FIG. 2, feedthrough 150 establishes electrical connections or pathways from body fluid side 138 to the interior space 134 of housing 132 while maintaining the integrity of hermetically sealed interior space 134 via conducting elements 154 which pass through insulator 152. According to one embodiment, insulator 152 is a glass or ceramic material, such as aluminum oxide ($Al_2O_3$). According to on embodiment, conducting elements 154 are formed of a cermet.

In the context of one embodiment, the terms, "cermet" or "cermet-containing," refers to composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or cermet-containing elements proceeds is the same as that for homogeneous powders, except that the metal is compacted more strongly at the same pressuring force as compared to the ceramic material. The cermet-containing bearing element has a higher thermal shock and oxidation resistance than sintered hard metals. In most cases, the ceramic components of the cermet are aluminum oxide ($Al_2O_3$) and zirconium dioxide ($ZrO_2$), whereas niobium, molybdenum, titanium, cobalt, zirconium, chromium and platinum are conceivable as metallic components.

According to one embodiment, such as illustrated by FIG. 3, the ceramic (e.g. $Al_2O_3$) of insulator 152 and the cermet of conducting elements 154 are formed in a first process such that an interface between insulator 152 and conducting elements 154 are hermetically sealed without the use of a braze or solder. According to one example of such an embodiment, the ceramic of insulator 152 is a multi-layer ceramic sheet into which a plurality of vias is introduced. The cermet of conducting elements 154 is then introduced into the vias. In one embodiment, both materials are introduced in a green state, and the combination is fired together. According to such an embodiment, the joining of insulator 152 with conducting elements 154 forms a hermetic seal without the use of braze or solder.

According to one embodiment, ultrasonic joint 180 is formed of a biocompatible bond material 166 and a metalized coating 164 between feedthrough 150 and housing 132. In one embodiment, the outside edges of insulator 152 are metalized (such as through a sputter coating process, for example) to provide a thin metal coating 164 thereon. In various embodiments, the insulator is metalized with biocompatible material such as gold, titanium, niobium, or various combinations thereof. Ultrasonic joint 180 formed of bond material 166 and metal coating 164 between feedthrough device 150 and metal housing 132 mechanically and hermetically couples feedthrough device 150 and metal housing 132. In one embodiment, bond material 166 is formed of a biocompatible metal. In various embodiments, gold, platinum, palladium, aluminum, niobium and combinations of these, may be used for bond material 166.

Figure 4:
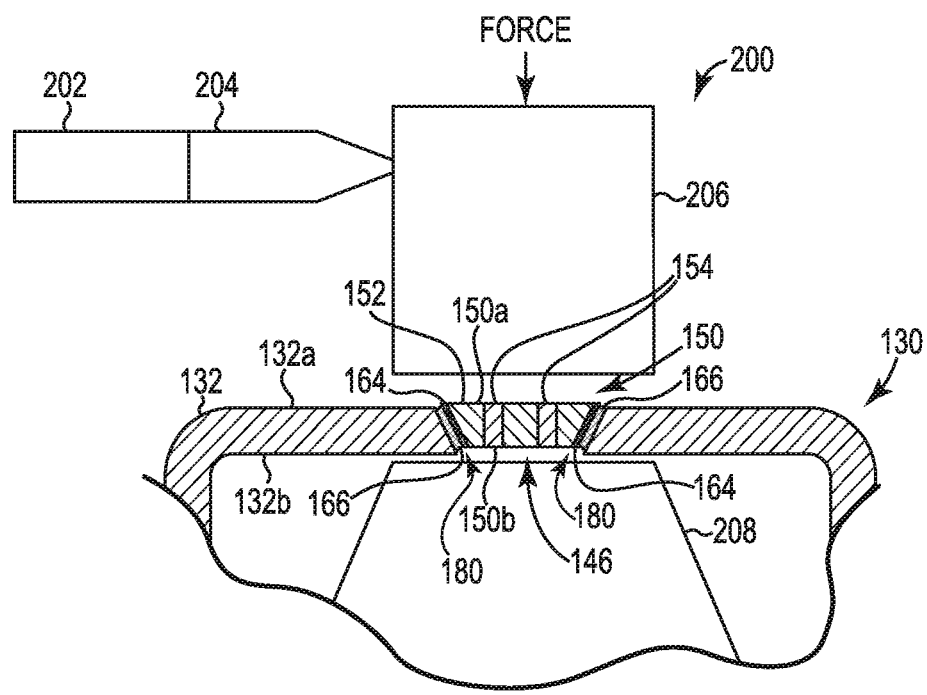
FIG. 4 illustrates a system for fabricating a feedthrough assembly in an implantable medical device in accordance with one embodiment.

FIG. 4 is a schematic diagram illustrating a system 200 for attaching feedthrough 150 to metal housing 132 according to one embodiment of the present disclosure. In one embodiment, system 200 is an ultrasonic welding system including transducer 202, coupler 204, sonotrode tip 206 and anvil 208. System 200 is configured to ultrasonically weld feedthrough 150 to metal housing 132 with a "cold welding" process to create ultrasonic joint 180, such that materials of feedthrough 150 and metal housing 132 stay well below the β-transus of those materials as feedthrough 150 and metal housing 132 are ultrasonically welded together.

In one embodiment, feedthrough 150, and specifically an outer edge of feedthrough 150, is metalized with thin metal coating 164. Feedthrough 150 is then placed within opening 146 of metal housing 132. Bond material 166 is placed in the interface between feedthrough 150 and metal housing 132 on both sides, and specifically between metal coating 164 on the outer edge of feedthrough 150 and metal housing 132.

Feedthrough 150 is then placed between anvil 208 on one side and sonotrode 206 on another as illustrated in FIG. 4. Sonotrode 206 and anvil 208 are then forced together such that feedthrough 150 and metal housing 132 are clamped therebetween, as is bond material 166, which fills the interface between them. Transducer 202 is then energized supplying ultrasonic energy to sonotrode 206 via coupler 204. Energizing sonotrode 206 causes vibration of feedthrough 150 and metal housing 132 and frictional forces at the interface between them such that a weld occurs at bond material 166 thereby joining feedthrough 150 and metal housing 132, mechanically and hermetically joining them.

In one embodiment, feedthrough 150 is bonded to metal housing 132 with bonding material 166 with ultrasonic welding using system 200. Ultrasonic vibration is used such that the materials are bonded without significantly raising the temperature of the materials above, or in one embodiment even near, the β-transus of the materials. As such, the grain size of the materials does not experience significant growth. In one example where metal housing 132 is titanium, the temperature of the metal housing 132 during ultrasonic welding is kept well below the around 880-890° C. β-transus temperature. In one case, the temperature during ultrasonic welding is kept below 750° C., and in another, below 400° C. In either case, the microstructure of the titanium remains primarily α-phase grains having an average grain size in the range of 10-40 μm and does not reach the β-transus, and does not experience significant grain growth such that there are no or minimal dimensional distortions of housing 132.

In various embodiments where feedthrough 150 is bonded to metal housing 132 with bonding material 166 using ultrasonic welding using system 200 such that a relatively low temperature is maintained during formation, metal housing 132 is a metal material with an average grain size in the range of less than 425 μm, less than 300 μm, less than 180 μm and less than 70 μm.

In one embodiment, the outside edges of feedthrough 150, which are metalized with thin metal coating 164 are angled relative to vertical and the inner edges of metal housing 132 are likewise angled to mirror the angle of the outside edges of feedthrough 150, as illustrated in FIG. 4. In this way, as sonotrode 206 and anvil 208 are forced together on either side of feedthrough 150 and metal housing 132, the angled edges facilitates the application of force to the interface between feedthrough 150 and metal housing 132 and the welding of bond material 166 into ultrasonic joint 180. In one embodiment, bond material 166 is a very thin layer, for example, the layer is less than 100 um.

In the embodiment illustrated in FIG. 4, metal housing 132 is sloped inward, such that opening 146 is smaller at interior space 134 side than at body fluid side 138. Feedthrough 150 is then shaped to compliment this slope and is wider at body fluid side 138 and narrower at interior space side 134. Also, an outer surface 150a of feedthrough 150 is displaced relative to an outer surface 132a of metal housing 132, such that when force is applied to sonotrode 206 toward feedthrough 150 and metal housing 132, sonotrode 206 will only contact feedthrough 150, but will not contact housing 132. Correspondingly, an inner surface 150b of feedthrough 150 is also displaced relative to an inner surface 132b of metal housing 132, such that when force is applied to anvil 208 toward feedthrough 150 and metal housing 132, anvil 208 will only contact housing 132, but will not contact feedthrough 150.

In this way, feedthrough 150 is forced against the angled edge of housing 132 as sonotrode 206 and anvil 208 are forced together. This force at the interface between feedthrough 150 and housing 132 facilitates ultrasonic joint 180 as system 200 is energized. A similar force can be created at the interface by inverting the slope of the edges of both feedthrough 150 and housing 132 and also inverting the relative displacement of the two, that is, outer surface 150a of feedthrough 150 is displaced "down" (as depicted in FIG. 4) relative to outer surface 132a of metal housing 132, such that when force is applied to sonotrode 206 toward feedthrough 150 and metal housing 132, sonotrode 206 will only contact housing 132, but will not contact feedthrough 150 and inner surface 150b of feedthrough 150 is displaced "down" (as depicted in FIG. 4) relative to inner surface 132b of metal housing 132, such that when force is applied to anvil 208 toward feedthrough 150 and metal housing 132, anvil 208 will only contact feedthrough 150, but will not contact housing 132.

According to one embodiment, feedthrough 150 has a width $W_{150}$ at a widest point between opposing sloped surfaces that is wider than a width $W_{146}$ of opening 146 in housing 132 (illustrated in FIG. 3), thereby creating an overlap between feedthrough 150 and housing 132. In this way, when a force is applied on either side of feedthrough 150 and housing 132 by sonotrode 206 and anvil 208 as described above, the force is transferred to the interface between feedthrough 150 and housing 132 thereby allowing the formation of ultrasonic joint 180. According to one embodiment, ultrasonic joint 180 has a thickness $T_{180}$. According to one embodiment, the thickness $T_{180}$ of ultrasonic joint 180 is in a range from 20 to 200 μm.

Figure 5:
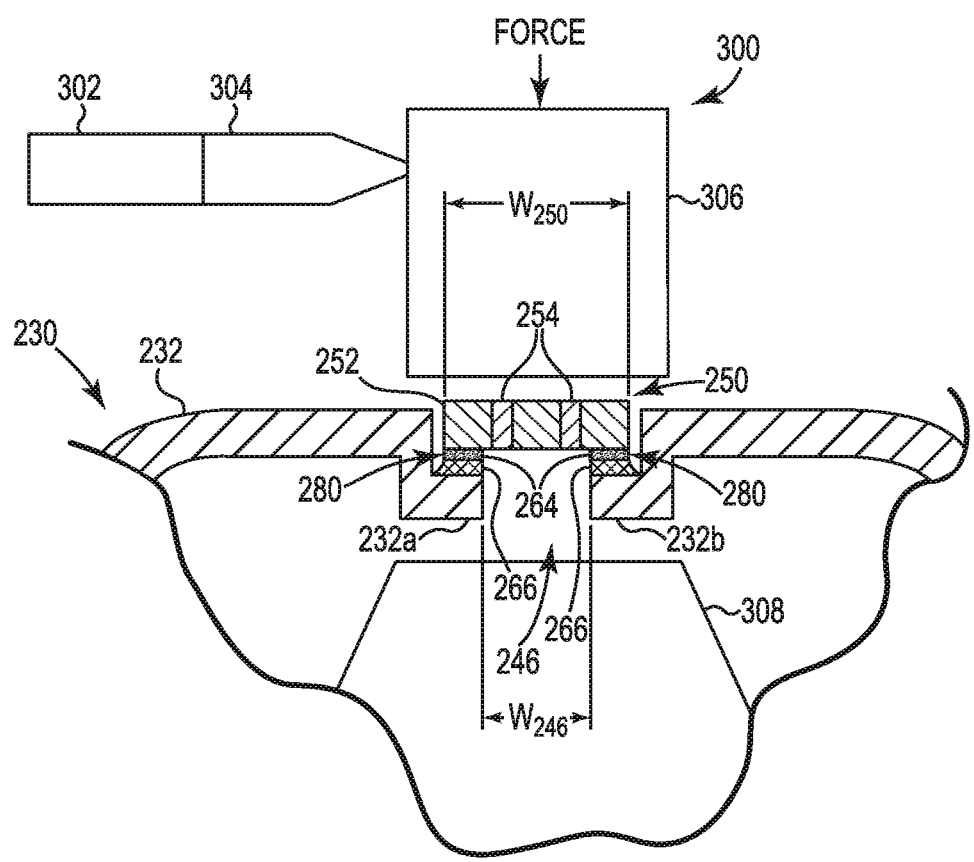
FIG. 5 illustrates a system for fabricating a feedthrough assembly in an implantable medical device in accordance with one embodiment.

FIG. 5 is a schematic diagram illustrating a system 300 for attaching feedthrough 250 to metal housing 232 for an implantable medical device 230 according to one embodiment of the present disclosure. In one embodiment, system 300 is an ultrasonic welding system including transducer 302, coupler 304, sonotrode tip 306 and anvil 308. System 300 is configured to ultrasonically weld feedthrough 250 to metal housing 232 with a "cold welding" process such that materials of feedthrough 250 and metal housing 232 stay well below the β-transus of the materials.

In one embodiment, a lower surface of feedthrough 250 is metalized with thin metal coating 264. Feedthrough 250 is then placed within opening 246 of metal housing 232. Furthermore, metal housing 232 is provided with first and second features 232a and 232b, which in one embodiment are ledge-like projections onto which feedthrough 250 can be placed. Bond material 266 is placed in the interface between feedthrough 250 and first and second features 232a and 232b of metal housing 232.

Feedthrough 250 is then placed between anvil 308 on one side and sonotrode 306 on another as illustrated in FIG. 5. Sonotrode 306 and anvil 308 are then forced together such that feedthrough 250 and metal housing 232 are clamped therebetween, as is bond material 266, which fills the interface between them. Transducer 302 is then energized supplying ultrasonic energy to sonotrode 306 via coupler 304. Energizing sonotrode 306 causes vibration of feedthrough 250 and metal housing 232 and frictional forces at the interface between them such that a weld occurs at bond material 266 thereby forming ultrasonic joint 280 joining feedthrough 250 and metal housing 232, mechanically and hermetically joining them.

As above, in one embodiment, feedthrough 250 is bonded to metal housing 232 with bonding material 266 using ultrasonic welding using system 300 with ultrasonic vibration such that the materials are bonded without significantly raising the temperature of the materials above, or in one embodiment even near, the β-transus of the materials. As such, the grain size of the materials does not experience significant growth as discussed above. As above, in various embodiments where feedthrough 250 is bonded to metal housing 232 with bonding material 266 using ultrasonic welding using system 300 such that a relatively low temperature is maintained during formation, metal housing 232 is a metal material with an average grain size in the range of less than 425 μm, less than 300 μm, less than 180 μm and less than 70 μm.

In one embodiment, first and second features 232a and 232b of metal housing 232 jog down from a profile of housing 232 and define opening 246 therebetween. As such, features 232a/232b provide a "ledge" against which feedthrough 250 can rest. Bond material 264 is easily added between feedthrough 250 and features 232a/232b at their interface, as illustrated in FIG. 5. In this way, as sonotrode 306 and anvil 308 are forced together on either side of feedthrough 250 and metal housing 232, the configuration of features 232a/232b facilitates the application of force to the interface between feedthrough 250 and metal housing 232 and the welding of bond material 266. In one embodiment, the bond material is a very thin layer, for example, the layer is less than 100 um. Other configurations of first and second features 232a and 232b are also possible. Also, features can be added to feedthrough 250 that are useful for mating with housing 232 and that will allow force applied by system 300 to facilitate ultrasonic welding at the interface.

According to one embodiment, feedthrough 250 has a width $W_{250}$ at its opposing outer surfaces that is wider than a width $W_{246}$ of opening 246 in housing 232, thereby creating an overlap between feedthrough 250 and housing 232. In this way, when a force is applied on either side of feedthrough 250 and housing 232 by sonotrode 306 and anvil 308 as described above, the force is transferred to the interface between feedthrough 250 and housing 232 thereby allowing the formation of ultrasonic joint 280. According to one embodiment, ultrasonic joint 280 has a total width that is defined by the width $W_{250}$ of feedthrough less the width $W_{246}$ of opening 246. This total width of ultrasonic joint 280 is split on either side of opening 246. In one embodiment, the width $W_{250}$ of feedthrough is at least twice the width $W_{246}$ of opening 246 such that the total width of ultrasonic joint 280 is sufficient to create a good hermetic seal. According to one embodiment, ultrasonic joint 280 has a thickness $T_{280}$, which in one embodiment, is in a range from 20 to 200 μm.

Figure 6:
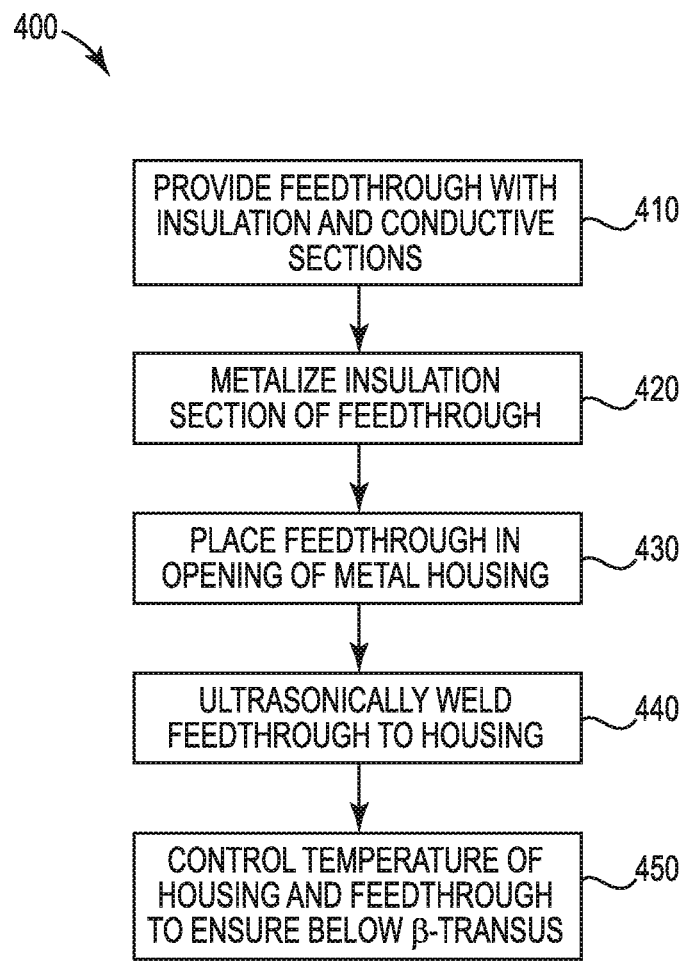
FIG. 6 illustrates a method for fabricating a feedthrough assembly in an implantable medical device in accordance with one embodiment.

FIG. 6 illustrates a method 400 of securing a feedthrough, such as feedthroughs 150 and 250 above, to a housing, such as metal housing 132 or 232 above, for an implantable medical device. At 410, a feedthrough 150/250 is provided comprising an insulating section and at least one conductive section extending through the insulating section. In one example, the conductive section is a cermet conductor extending through the insulator, which is a ceramic material.

At 420, at least the insulator 152/252 of the feedthrough 150/250 is metalized with a metal coating 164/264. In one example, the metallization is a sputter coating process. At 430, the feedthrough 150/250 is placed in an opening of metal housing 132/232. In one embodiment, feedthrough 150/250 and the opening of metal housing 132/232 are configured with features that are symmetrical such that they fit together along an interface defined by the features. Furthermore, one or more bonding materials can be placed in the interface between them.

At 440, the combination of the feedthrough 150/250 and the metal housing 132/232 are positioned within an ultrasonic welding system and the ultrasonic welding system is energized such that sonic energy welds the feedthrough 150/250 directly to the metal housing 132/232. At 450, the system is controlled such that the temperature of the materials of the metal housing and feedthrough are not raised above the β-transus temperature of the materials during the welding.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An implantable medical device comprising:
   a metal housing configured for implantation in a human and comprising a biocompatible metal and defining an opening;
   a feedthrough device configured within the opening of the metal housing and comprising an insulating section and a conducting section, the insulating section electrically isolating the conducting section from the metal housing; and
   an ultrasonic joint between the feedthrough device and metal housing that hermetically and mechanically bonds the feedthrough device directly to the metal housing without any intervening ferrule;
   characterized in that the biocompatible metal of the housing comprises a microstructure primarily having α-phase grains.

2. The implantable medical device of claim 1, further characterized in that the biocompatible metal of the housing comprises a microstructure having substantially no β-phase grains.

3. The implantable medical device of claim 1, further comprising a biocompatible bonding material between the feedthrough device and metal housing.

4. The implantable medical device of claim 1, wherein the biocompatible metal of the housing comprises titanium, niobium or a combination thereof.

5. The implantable medical device of claim 1, wherein the biocompatible metal of the housing has an average grain size less than 425 μm.

6. The implantable medical device of claim 1, wherein the biocompatible metal of the housing has an average grain size less than 300 μm.

7. The implantable medical device of claim 1, wherein the biocompatible metal of the housing has an average grain size less than 100 μm.

8. The implantable medical device of claim 1, wherein the biocompatible metal of the housing has an average grain size in the range of 10-40 μm.

9. The implantable medical device of claim 1, wherein an interface between the feedthrough and metal housing is substantially angled relative an exterior surface of the metal housing.

10. The implantable medical device of claim 1, wherein a width on the opening of the housing is smaller than a width of the feedthrough device at its widest distance between two opposing sides.

11. An implantable medical device comprising:
    a housing having an opening with an opening width;
    a feedthrough including an insulator having a bottom surface and side surfaces and having an insulator width between opposing side surfaces that is greater than the opening width; and a ultrasonic joint between at least one of the bottom surface, top surface, and side surfaces of the insulator and the housing which hermetically seals the insulator directly to the housing without any intervening ferrule.

12. The implantable medical device of claim 11, wherein the insulator width between opposing side surfaces is two times greater than the opening width.

13. The implantable medical device of claim 11, characterized in that the housing comprises a biocompatible metal comprising a microstructure primarily having α-phase grains.

14. The implantable medical device of claim 13, characterized in that the biocompatible metal of the housing comprises a microstructure having substantially no β-phase grains.

15. The implantable medical device of claim 11, wherein the housing comprises a metal having an average grain size less than 300 μm.

16. The implantable medical device of claim 11, wherein the biocompatible metal of the housing has an average grain size less than 100 μm.

17. The implantable medical device of claim 11, wherein the biocompatible metal of the housing has an average grain size in the range of 10-40 μm.

* * * * *